United States Patent [19]

König et al.

[11] Patent Number: 4,658,016
[45] Date of Patent: Apr. 14, 1987

[54] PROCESS FOR THE PREPARATION OF PENTAPEPTIDES HAVING AN ACTION ON THE IMMUNE SYSTEM AND INTERMEDIATE PRODUCTS FOR THIS PROCESS

[75] Inventors: Wolfgang König, Hofheim am Taunus; Rolf Geiger, Frankfurt am Main; Rainer Obermeier, Hattersheim am Main; Hubert Müllner, Kelkheim, all of Fed. Rep. of Germany

[73] Assignee: Hoechst Aktiengesellschaft, Frankfurt, Fed. Rep. of Germany

[21] Appl. No.: 742,441

[22] Filed: Jun. 7, 1985

[30] Foreign Application Priority Data

Jun. 9, 1984 [DE] Fed. Rep. of Germany ....... 3421614

[51] Int. Cl.$^4$ .......................... C07K 1/02; C07K 7/06
[52] U.S. Cl. .................................... 530/330; 530/339
[58] Field of Search ................. 260/112.5 R; 530/330, 530/339

[56] References Cited

U.S. PATENT DOCUMENTS 4,420,424 12/1983 Geiger et al. ................. 260/112.5 R
4,510,082 4/1985 Gesellchen et al. .......... 260/112.5 R

OTHER PUBLICATIONS

Ber. dtsch. Chem. Ges. 65, 1192 (1932).
J. Org. Chem. 44, 3442 (1979).
J. Org. Chem. 43 4194 (1978).
The Chem. Ber. 103, 2034, and 788 (1970).
Z. Naturforsch 21b, 426 (1966).
Chem. Pharm. Bull. 22 1857 (1974).

Primary Examiner—Delbert R. Phillips
Attorney, Agent, or Firm—Finnegan, Henderson, Farabow, Garrett & Dunner

[57] ABSTRACT

The invention relates to a process for the preparation of peptides of the general formula

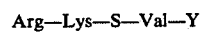

in which S denotes glutamic acid or α-aminoadipic acid and Y denotes tyrosine or tryptophan or esters or amides thereof, which comprises subjecting tetrapeptides of the formula

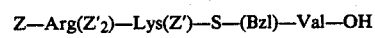

in which Z' represents a protective group of the benzyl type, to a condensation reaction with corresponding tyrosine esters or amides or tryptophan esters or amides and removing the protective groups by hydrogenation. The invention furthermore relates to tetrapeptides as intermediate products of this process.

5 Claims, No Drawings

PROCESS FOR THE PREPARATION OF PENTAPEPTIDES HAVING AN ACTION ON THE IMMUNE SYSTEM AND INTERMEDIATE PRODUCTS FOR THIS PROCESS

Peptides of the general formula

A—B—S—X—Y in which
- A denotes arginine, lysine, ornithine or homoarginine, in each case in the L- or D-configuration, or ω-amino-, -quanidino- or -dimethylanino-alkanoyl with 3 to 6 carbon atoms and, if appropriate, an α-amino group, in the D- or L-configuration, which can in turn carry alkanoyl with 1 to 6 carbon atoms, aroyl with 7 to 11 carbon atoms, cycloalkanoyl with up to 2 alkyl and 5 to 7 cycloalkyl carbon atoms, aralkanoyl with up to a total of 9 carbon atoms, it being possible for one —CH$_2$— group to be replaced by —O— or —S—, alkyl- or aralkyl-oxycarbonyl with up to 7 carbon atoms or succinyl, succinamyl, glutaryl, glutaminyl, pyroglutamyl, phthalyl, phthalamidyl or 2-carboxybenzoyl,
- B denotes a basic aminoacid, preferably L-lysine, L-arginine, L-homoarginine or L-ornithine,
- S denotes L-glutamic acid, D-glutamic acid, D-asparaginic acid or D- -aminoadipic acid,
- X denotes L-valine or L-isoleucine and
- Y denotes an amino acid with a hydrophobic side chain in the L- or D-configuration, such as, for example, tryptophan or tyrosine or their esters, amides, alkylamides with 1 to 6 carbon atoms or aralkylamides with 7 to 10 carbon atoms, alkylamide or alkyl ester with 1 to 6 carbon atoms or aralkylamide or aralkyl ester with 7 to 10 carbon atoms, and processes for their preparation are known from U.S. Pat. No. 4,420,424.

Under the synthesis conditions of known processes, tryptophan in particular, but also tyrosine, tends to form by-products.

There was thus the object of finding synthesis routes for the preparation of peptides containing tryptophan or tyrosine which result in few by-products.

This object was achieved by the process according to the invention for the preparation of peptides of the general formula Arg—Lys—S—Val—Y in which
- S denotes glutamic acid or α-aminoadipic acid, in each case in the L- or D-configuration, and
- Y denotes tyrosine or tryptophan, in each case in the L- or D-configuration, or their esters, amides, alkylamides, cycloalkylamides or aralkylamides, which comprises subjecting tetrapeptides of the formula Z—Arg(Z'$_2$)—Lys(Z')—S(Bzl)—Val-OH in which S is as defined above and Z' represents an amino-protective group of the benzyl type, to a condensation reaction with corresponding tyrosine esters or amides or tryptophan esters or amides and splitting off the protective groups of the benzyl type by catalytic hydrogenation or by catalytic transfer hydrogenation, for example with formic acid. Bzl represents benzyl or modified benzyl ester-protective groups, such as p-chloro-, p-bromo- or p-nitro-benzyl.

This concept enables tryptophan or tyrosine to be introduced into the peptide only at the end. Equation 1 shows the synthesis equation for these peptides. If the free carboxyl group is desired on the terminal C atom, the benzyloxy group is recommended for R. These protective groups of the benzyl type can be split off together.

However, the synthesis principle according to the invention is not restricted to the synthesis of peptides of the formula Arg—Lys—S—Val—Y, but it is quite generally applicable to the synthesis of peptides of the formula A—B—S—X—Y defined above, in which Y denotes tyrosine or tryptophan.

Equation 1

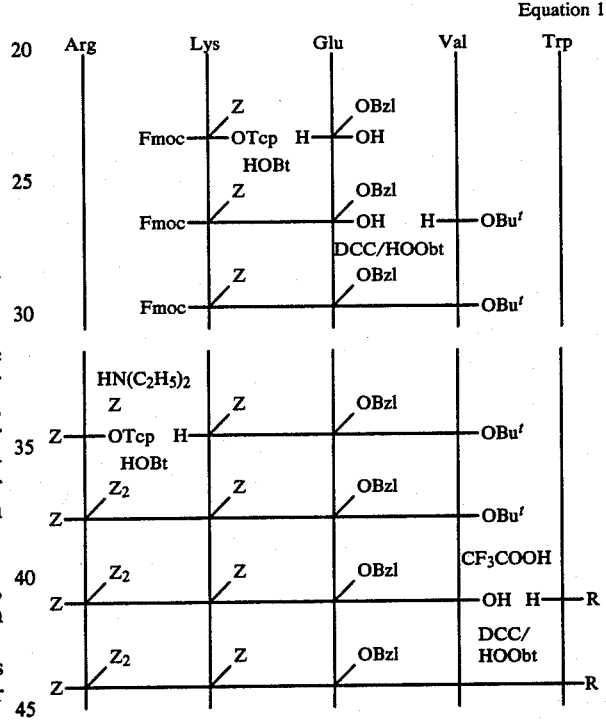

Protective groups of the benzyl type (Z') are understood in this connection as being, for example, benzyloxycarbonyl (Z), Z(NO$_2$), Z(Hal)$_n$ and Moc, but in particular benzyloxycarbonyl (in this context, c.f., for example, Hubbuch, Kontakte Merck (Merck Contacts) 3/79, page 14 et seq.).

C-terminal ester groups of the pentapeptides from the process according to the invention are preferably (C$_1$–C$_6$)-alkyl or (C$_3$ to C$_8$)-cycloalkyl ester groups. C-terminal (C$_1$ to C$_6$)-alkylamide, (C$_3$ to C$_8$)-cycloalkylamide and (C$_7$ to C$_{10}$)-aralkylamide groups (for example benzylamide) are also preferred.

The protective groups Z' are split off by catalytic hydrogenation in dimethylformamide, dimethylacetamide or acetic acid (Ber. dtsch. chem. Ges. 65, 1192 (1932)) or by catalytic transfer hydrogenation, for example with formic acid (J. Org. Chem. 44, 3442 (1979)) or with cyclohexadiene (J. Org. Chem. 43, 4194 (1978)).

Catalytic transfer hydrogenation in formic acid/dimethylformamide or dimethylacetamide mixtures above all has proved particularly advantageous in the case of the protective sparingly soluble peptides described here. Thus, for example, it was not possible to deblock Z—Arg($Z_2$)—Lys(Z)—Glu(OBzl)—Val—Trp—OBzl by catalytic hydrogenation without trouble. In contrast, the protective groups were removed without problems with palladium in dimethylformamide/formic acid solution.

Methods in which the risk of racemization is low are used for the condensation. The dicyclohexylcarbodiimide/3-hydroxy-4-oxo-3,4-dihydro-1,2,3-benzotriazine (DCC/HOObt) method was used here (Chem. Ber. 103, 2034 (1970)). However, other racemization-reducing additives to the DCC, such as, for example, 1-hydroxybenzotriazole (Chem. Ber. 103, 788 (1970), N-hydroxysuccinimide (Z. Naturforsch. 21b, 426 (1966)) or N-hydroxy-5-norborneneendo-2,3-dicarboximide (Chem. Pharm. Bull. 22, 1857 (1974)) are also possible.

After the protective groups have been split off, the peptide formates thus formed are converted into the acetates, for example, by treatment with weakly basic ion exchangers (in the acetate form), and the acetates can then be purified in the customary manner.

The invention also relates to tetrapeptides of the formula Z'—Arg($Z'_2$)—Lys(Z')—S(OBzl)—Val—OH, in which S and Z' are as defined above, and to processes for their preparation by fragment condensation.

In vitro and in the presence of liver homogenates, the peptides according to the invention have a considerably prolonged life, compared with natural thymus peptides. The compounds in which S is represented by an acid D-aminoacid, such as D-glutamic acid or D-α-aminoadipic acid, should be singled out particularly. Their action can be demonstrated, for example, in vitro by their effect on T-lymphocytes which form SRBC rosettes, from the blood of patients deficient in immunity or human umbilical cord blood analogously to the methods of J. Exptl. Med. 136 (1972) page 207; Anm. N. Y. Acad. Sci. 249 (1975) page 308 and Int. Archs. Allergy appl. Immun. 53 (1977) page 242, and also their effect on the PHA-induced lymphoblast transformation of human and animal lymphocytes analogously to the methods of J. Exptl. Med. 131 (1970), page 1049, and Cell. Immunol. 16 (1975), page 413. (SRBC=sheep red blood cell; PHA=phytohaemagglutinin).

The compounds according to the invention can be used for treating deficiencies of immunity, viral and fungoid, and also chronic bacterial infections and auto-immunity diseases, and also for the therapy of illnesses caused by cells having immunologically relevant changes in the cell membrane characteristics (for example tumor cells).

In this sense the present invention relates also to the use of the above peptides to influence generally the maturation of T-lymphocytes.

The examples which now follow serve to illustrate the invention, without restricting it thereto.

EXAMPLE 1

(a)

Fmoc—Lys(Z)—OH 35.38 g (105 mmol) of Fmoc—ONSu are added to a suspension of 28 g (100 mmol) of H—Lys(Z)—OH and 16.8 g (200 mmol) of $NaHCO_3$ in a mixture of 200 ml of water and 200 ml of dioxane. The mixture is stirred at room temperature for about 24 hours. The undissolved material is filtered off with suction and the filtrate is concentrated. The residue is partitioned between 300 ml of 1N HCl and ethyl acetate. The ethyl acetate phase is extracted by shaking with water, dried over $Na_2SO_4$ and concentrated. The resulting oil is dissolved in 200 ml of ether. The product crystallizes by addition of 200 ml of petroleum ether. The precipitate is filtered off with suction and triturated again with ether.

Yield: 34.05 g (68%), melting point: 110°–112° C., $[\alpha]_D^{22} = +6.5°$ (c=1, in tetrahydrofuran).

(b)

Fmoc—Lys(Z)—OTcp 5.76 g (28 mmol) of DCC are added to a solution of 12.55 g (25 mmol) of Fmoc—Lys(Z)—OH and 4.92 g (25 mmol) of 2,4,5-trichlorophenol in 100 ml of tetrahydrofuran at 0° C. The mixture is stirred at 0° C. for one hour and left to stand overnight at room temperature. The precipitate is filtered off with suction and the filtrate is concentrated. The resulting oil is digested twice with petroleum ether. The substance, which meanwhile becomes semi-solid, is triturated with ether, filtered off with suction and dried.

Yield: 12.36 g (72%), melting point: 107°–108° C., $[\alpha]_D^{22} = -15.4°$ (c=1, in ethyl acetate).

(c)

Fmoc—Lys(Z)—Glu(OBzl)—OH 17.7 g (26 mmol) of Fmoc—Lys(Z)—OTcp are added to a suspension of 6.6 g (26 mmol) of H—Glu(OBzl)—OH and 3.5 g of HOBt in 50 ml of dimethylformamide at room temperature, with stirring. The mixture is stirred at room temperature for 4 hours and left to stand overnight. The solution is concentrated and the residue is dissolved in 150 ml of ethanol under the influence of heat. The solution is cooled and the precipitate is filtered off with suction. For further purification, the precipitate is stirred with water. It is then filtered off with suction and dried in vacuo over $P_2O_5$.

Yield: 15 g (79.9%), melting point: 156° C., $[\alpha]_D^{22} = -9.6°$ (c=1, in methanol).

(d)

Fmoc—Lys(Z)—Glu(OBzl)—Val—OBu$^t$ 2.6 ml of N-ethylmorpholine and 4.4 g of DCC are added to a solution of 14.4 g (20 mmol) of Fmoc—Lys(Z)—Glu(OBzl)—OH, 3.26 g of HOObt and 4.2 g of H—Val—OBu$^t$·HCl in 50 ml of dimethylformamide at 0° C. The mixture is stirred at 0° C. for two hours and left to stand overnight at room temperature. The precipitate is filtered off with suction and 150 ml of water and 10 ml of saturated $NaHCO_3$ solution are added to the filtrate. This second precipitate is filtered off with suction, washed with water and dried.

Yield: 18 g.

For further purification, the substance is purified on 150 g of silica gel. The column is eluted first with methylene chloride and a little methanol (1–3%) is then added to the eluting agent.

Yield: 12.55 g (71.5%), melting point: 181°–182° C., $[\alpha]_D^{22} = -35°$ (c=1, in methanol).

(e)

Z—Arg($Z_2$)—Lys(Z)—Glu(OBzl)—Val—OBu$^t$ 14.5 ml (140 mmol) of diethylamine are added to a solution of 12.28 g (14 mmol) of Fmoc—Lys(Z)—Glu(OBzl)—Val—OBu$^t$ in 140 ml of dimthylformamide. The mixture is stirred at room temperature for 5 minutes and concentrated. The residue is chromatographed on silica gel. Lipophilic by-products are first eluted with methylene chloride. The substance is eluted with a 9:1:0:1 methylene chloride/methanol/water mixture and the corresponding fractions are concentrated.

Yield: 9.2 g

The residue is dissolved in 40 ml of dimethylformamide together with 2 g of HOBt. 12.5 g of Z—Arg(Z$_2$)—OTcp are added to this solution, with stirring. After a few hours, the batch becomes solid. The sludge is stirred with 120 ml of water and 14 ml of saturated NaHCO$_3$ solution. The precipitate is filtered off with suction, washed with water and dried over P$_2$O$_5$. For purification, the substance is boiled up with methanol and filtered off with suction.

Yield: 15.5 g (91%), melting point: 184°–185° C., $[\alpha]_D^{22} = -9.2°$ (c=1, in dimethylformamide).

(f)

Z—Arg(Z$_2$)—Lys(Z)—Glu(OBzl)—Val—OH 15 g (12.36 mmol) of Z—Arg(Z$_2$)—Lys(Z)—Glu(OBzl)—Val—OBu$^t$ are dissolved in 150 ml of 90% strength (aqueous) trifluoroacetic acid. After one hour, the solution is concentrated. The residue is triturated with ether, filtered off with suction and dried.

Yield: 15.5 g.

For purification, the substance is boiled up with 200 ml of ethyl acetate, filtered off with suction and dried.

Yield: 11.9 g (83.2%), melting point: 177°–178° C., $[\alpha]_D^{22} = -10.2°$ (c=1, formic acid).

(g)

Z—Arg(Z$_2$)—Lys(Z)—Glu(OBzl)—Val—Trp—OBzl 1.69 ml of N-ethylmorpholine and 2.85 g of DCC are added to a solution of 15 g (12.96 mmol) of Z—Arg(Z$_2$)—Lys(Z)—Glu(OBzl)—Val—OH, 2.11 g of HOObt and 6.05 g of H—Trp—OBzl.Tos—OH in 130 ml of dimethylformamide at 0° C. The mixture is stirred at 0° C. for two hours and then at room temperature for four hours. It is left to stand overnight at room temperature and the precipitate is filtered off with suction. 650 ml of water and 13 ml of saturated NaHCO$_3$ solution are added to the filtrate. The precipitate is filtered off with suction, washed with water and dried.

Yield: 19.4 g.

For purification, the substance is boiled up with 500 ml of ethyl acetate, filtered off with suction and dried.

Yield: 15.1 g (81.3%), melting point: 203°–204°, $[\alpha]_D^{22} = -18.1°$ (c=1, formic acid).

(h)

H—Arg—Lys—Glu—Val—Trp—OH . CH$_3$COOH 50 ml of dimethylformamide are added to a solution of 10 g (about 7 mmol) of Z—Arg(Z$_2$)—Lys(Z)—Glu—(OBzl)—Val—Trp—OBzl in 50 ml of formic acid. The mixture is covered with a layer of N$_2$ and Pd/charcoal catalyst is added. If the reaction does not start up correctly, further catalyst is added after some time. After all the protective groups have been split off (2 to 3 hours), the catalyst is filtered off with suction and the filtrate is concentrated. The residue is dissolved in water and the solution is stirred with an ion exchanger (IRA 93, acetate form). The ion exchanger is filtered off with suction and, finally, is washed with a little dilute acetic acid until the eluate is free from peptide. The eluate is concentrated or freeze-dried and the residue is purified by column chromatography.

Yield: about 3.5 g, $[\alpha]_D^{22} = -31.8°$ (c=1, in water).

EXAMPLE 2

(a)

Z—Arg(Z$_2$)—Lys(Z)—Glu(OBzl)—Val—Trp isobutylamide 0.13 ml of N-ethylmorpholine and 0.22 g of DCC are added to a solution of 1.16 g (1 mmol) of Z—Arg(Z$_2$)—Lys(Z)—Glu(OBzl)—Val—OH, 0.296 g (1 mmol) of H—Trp isobutylamide hydrochloride and 0.163 g (1 mmol) of HOObt at 0° C. The mixture is stirred at 0° C. for two hours and then left to stand overnight at room temperature. The batch solidifies as a gel. The batch is stirred with 50 ml of water and 1 ml of saturated NaHCO$_3$ and the product is filtered off with suction. The product is washed with water and dried over P$_2$O$_5$.

Yield: 1.55 g.

The product is then boiled up with ethyl acetate, cooled and filtered off with suction.

Yield: 1.42 g (the substance still contains dicyclohexylurea), melting point: 210°–212° C., $[\alpha]_D^{22} = -10.4°$ (c=1, in dimethylformamide).

(b)

Arg—Lys—Glu—Val—Trp isobutylamide diacetate 1.4 g of the substance obtained under Example 2a (about 0.87 mmol of Z—Arg(Z$_2$)—Lys(Z)—Glu(OBzl)—Val—Trp isobutylamide) are dissolved in 100 ml of dimethyl acetate under the influence of heat. 3.34 ml of acetic acid, 10 ml of water and Pd/charcoal catalyst are added. Hydrogen is passed through the solution. When the hydrogenation has ended (TLC check), the catalyst is filtered off with suction and the filtrate is concentrated. The residue is purified by column chromatography.

Yield: 359 mg (peptide base content according to amino acid analysis: about 70%) (46%).
$[\alpha]_D^{23} = -34.7°$ (c=1, water).

EXAMPLE 3

(a)

Z—Arg(Z$_2$)—Lys(Z)—Glu(OBzl)—Val—Trp cyclohexyl ester 1.16 g (1 mmol) of Z—Arg(Z$_2$)—Lys(Z)—Glu(OBzl)—Val—OH and 0.323 g (1 mmol) of H-Trp cyclohexyl ester hydrochloride are reacted analogously to Example 2a. The dicyclohexylurea which has precipitated is filtered off with suction and 50 ml of water and 1 ml of an aqueous saturated NaHCO$_3$ solution are added to the filtrate. Further working up is analogous to Example 2a.

Yield: 1.23 g (86%), melting point: 205°–206° C., $[\alpha]_D^{23} = -5.6°$ (c=1, in dimethylformamide).

(b)

Arg—Lys—Glu—Val—Trp cyclohexyl ester diacetate

Analogously to Example 2b, 1.2 g (0.84 mmol) of Z—Arg(Z$_2$)—Lys(Z)—Glu(OBzl)—Val—Trp cyclohexyl ester are catalytically hydrogenated and the product is purified.

Yield: 505 mg (peptide content according to amino acid analysis: about 70%) (44%), $[\alpha]_D^{23} = -36.3°$ (c=1, in water).

EXAMPLE 4

(a)

Fmoc—Lys(Z)—D—Aad(OBzl)—OH 8.5 g of HOBt and 42.7 g (62.5 mmol) of Fmoc—Lys(Z)—OTcp are added to a suspension of 15.7 g (62.5 mmol) of H—Aad(OBzl)—OH in 125 ml of dimethylformamide. The mixture is stirred at room temperature for 8 hours and at 5° C. for two days. The batch is then solidified. It is triturated with 800 ml of diethyl ether and the product is filtered off with suction and rinsed with ether.

Yield: 35.9 g (78%), melting point: 138°-139° C.

(b)

Fmoc—Lys(Z)—D—Aad(OBzl)—Val—OBu$^t$ 6.2 ml of N-ethylmorpholine and 10.45 g of DCC in 50 ml of dimethylformamide are added to a suspension of 34.95 g (47.5 mmol) of Fmoc—Lys(Z)—D—Aad-(OBzl)—OH, 9.98 g (47.5 mmol) of H—Val—OBu$^t$, 9.98 g (47.5 mmol) of H—Val—OBu$^t$.HCl and 7.75 g of HOObt in 200 ml of dimethylformamide at 0° C. The mixture is worked up analogously to Example 1d. For purification, the still moist substance is dissolved in 300 ml of hot ethyl acetate. The ethyl acetate solution is dried with Na$_2$SO$_4$ under the influence of heat and the Na$_2$SO$_4$ is filtered off hot. A substance is precipitated from the ethyl acetate solution with 900 ml of petroleum ether. The precipitate is filtered off with suction and dissolved in 300 ml of isopropanol under the influence of heat. The solution is left to stand overnight at 4° C. and the precipitate is filtered off with suction.

Yield: 31 g (87.1%), melting point: 120°-122° C.

(c)

Z—Arg(Z$_2$)—Lys(Z)—D—Aad(OBzl)—Val—OBu$^t$ 30.34 g (40.5 mmol) of Fmoc—Lys(Z)—D—Aad-(OBzl)—Val—OBu$^t$ are treated with 162 ml (405 mmol) of diethylamine in 405 ml of dimethylformamide analogously to Example 1e.

Yield: 18.5 g (68.3%).

This residue is reacted with 21 g (27.6 mmol) of Z—Arg(Z$_2$)—OTcp and 3.7 g of HOBt analogously to Example 1e. After two hours, the batch solidifies as a gel. It is triturated with 200 ml of water and 28 ml of saturated NaHCO$_3$ solution and the product is filtered off with suction and washed with water. It is then boiled up with 300 ml of methanol and filtered off with suction.

Yield: 23.2 g (68.3%), melting point: 171°-172° C., $[\alpha]_D^{22} = +0.9°$ (c=1, in dimethylformamide).

(d)

Z—Arg(Z$_2$)—Lys(Z)—D—Aad(OBzl)—Val—OH 22.7 g (18.5 mmol) of Z—Arg(Z$_2$)—Lys(Z)—D—Aad(OBzl)—Val—OH are dissolved in 227 ml of 90% strength trifluoroacetic acid. The solution is left to stand at room temperature for one hour and is concentrated. The residue is triturated with ether, filtered off with suction and dried.

Yield: 19.1 g.

For purification, the substance is boiled up with 200 ml of methanol, filtered off with suction and dried.

Yield: 16.1 g (74.3%), melting point: 167°-168° C., $[\alpha]_D^{22} = -3.8°$ (c=1, formic acid).

(e)

Z—Arg(Z$_2$)—Lys(Z)—D—Aad(OBzl)—Val—Trp isobutylamide 1.17 g (1 mmol) of Z—Arg(Z$_2$)—Lys(Z)—D—Aad-(OBzl)—Val—OH are reacted with 0.296 g of H—Trp isobutylamide hydrochloride analogously to Example 2a. The dicyclohexylurea is filtered off with suction and 50 ml of water and 1 ml of saturated NaHCO$_3$ solution are added to the filtrate. The precipitate is filtered off with suction, washed with water and dried. For purification, it is boiled up with 50 ml of methanol, filtered off with suction and dried.

Yield: 1.21 g (85.6%), melting point: 203°-206° C., $[\alpha]_D = -11.2°$ (c=1, dimethylformamide).

(f)

Arg—Lys—D—Aad—Val—Trp isobutylamide diacetate 1 g of Z—Arg(Z$_2$)—Lys(Z)D—Aad(OBzl)—Val—Trp isobutylamide is dissolved in 5 ml of formic acid and 5 ml of dimethylformamide and, analogously to Example 1h, the solution is reacted and the product is purified.

Yield: 213 mg (content of peptide base according to amino acid analysis: 78%), $[\alpha]_D^{23} = -5°$ (c=1, in water).

EXAMPLE 5

(a)

Z—Arg(Z$_2$)—Lys(Z)—D—Aad(OBzl)—Val—Trp cyclohexyl ester 1.17 g (1 mmol) of Z—Arg(Z$_2$)—Lys(Z)—D—Aad-(OBzl)—Val—OH are reacted analogously to Example 3a. For purification, the substance is boiled up with 50 ml of methanol, filtered off with suction and dried.

Yield: 1.2 g (83.3%), $[\alpha]_D^{22} = -1.3°$ (c=1, dimethylformamide).

(b)

Arg—Lys—D—Aad—Val—Trp cyclohexyl ester diacetate

Analogously to Example 1h, 1.0 g of Z—Arg(Z$_2$)—Lys(Z)—D—Aad(OBzl)—Val—Trp cyclohexyl ester is reacted and the product is purified.

Yield: 343 mg (content of peptide base according to amino acid analysis: about 75%), $[\alpha]_D^{23} = -13.4°$ (c=1, water).

EXAMPLE 6

(a)

Z—Arg(Z$_2$)—Lys(Z)—D—Aad(OBzl)—Val—Tyr—OBzl 11.72 g (10 mmol) of Z—Arg(Z$_2$)—Lys(Z)—D—Aad—(OBzl)—Val—OH are reacted with 4.44 g (10 mmol) of H—Tyr—OBzl tosylate analogously to Example 1g. For purification, the substance is boiled u with 500 ml of methanol.

Yield: 12.6 g (88.4%), $[\alpha]_D^{22} = -0.4°$ (c=1, dimethylformamide).

(b)

Arg—Lys—D—Aad—Val—Tyr acetate

Analogously to Example 1h, 12 g of Z—Arg(Z$_2$)—Lys(Z)—D—Aad(OBzl)—Val—Tyr—OBzl are reacted and the product is purified.

Yield: 4.5 g (content of peptide base according to amino acid analysis: about 83.9%), $[\alpha]_D^{22} = +13°$ (c=1, water).

EXAMPLE 7

(a)

Z—Arg(Z$_2$)—Lys(Z)—D—Aad(OBzl)Val—Trp—OBzl 1.17 g (1 mmol) of Z—Arg(Z$_2$)—Lys(Z)—D—Aad(OBzl)—Val—OH are reacted with 0.466 g (1 mmol) of H—Trp—OBzl tosylate analogously to Example 1g. For purification, the substance is boiled up with 50 ml of methanol, filtered off with suction and dried.

Yield: 1.22 g (84.2%), $[\alpha]_D^{22} = +1.8°$ (c=1, dimethylformamide).

(b)

Arg—Lys—D—Aad—Val—Trp acetate

Analogously to Example 1h, 1 g of Z—Arg(Z$_2$)—Lys(Z)—D—Aad(OBzl)—Val—Trp—OBzl is reacted and the product is purified.

Yield: 291 mg (content of peptide base according to amino acid analysis: 84%), $[\alpha]_D^{23} = +3.30$ (c=1, water).

Abbreviations:
DCC: dicyclohexylcarbodiimide
HOObt: 3-hydroxy-4-oxo-3,4-dihydro-1,2,3-benzotriazine
HOBt: 1-hydroxybenzotriazole
OBu$^t$: tert.-butyl ester
OBzl: benzyl ester
Fmoc: 9-fluorenylmethoxycarbonyl
Z: benzyloxycarbonyl.

We claim:

1. A process for the preparation of a peptide of the formula

Arg—Lys—S—Val—Y wherein
S denotes glutamic acid or α-aminoadipic acid, in each case in the L- or D-configuration, and
Y denotes tyrosine or tryptophan, in each case in the L- or D-configuration, or their esters, amides, alkylamides, cycloalkylamides or aralkylamides, which comprises subjecting a tetrapeptide of the formula Z—Arg(Z')—Lys(Z')—S—(Bzl)—Val—OH in which S is as defined above and Z' represents an amino-protective group of the benzyl type, to a condensation reaction with the corresponding tyrosine ester or amide or tryptophan ester or amide and splitting off the protective groups of the benzyl type by catalytic transfer hydrogenation with formic acid/dimethylformamide or dimethylacetamide mixtures.

2. The tetrapeptide Z'—Arg(Z'$_2$)—Lys(Z')—S(OBzl)—Val—OH, in which S denotes glutamic acid or aminoadipic acid in the L- or D-configuration and Z' represents an amino-protective group of the benzyl type.

3. Peptide of the formula

Arg—Lys—S—Val—Y in which S is Glu and Y is Trp, or S is D—Aad and Y is Tyr and physiologically acceptable salts thereof.

4. Peptide as claimed in claim 3 which is

H—Arg—Lys—Glu—Val—Trp—OH and physiologically acceptable salts thereof.

5. Peptide as claimed in claim 3 which is

H—Arg—Lys—D—Aad—Val—Tyr—OH and physiologically acceptable salts thereof.

* * * * *